United States Patent [19]

Shinno et al.

[11] Patent Number: 4,695,276
[45] Date of Patent: Sep. 22, 1987

[54] MEDICAL INSTRUMENT

[75] Inventors: Kouji Shinno, Yamanashi; Hitoshi Kuboki, Kofu, both of Japan

[73] Assignee: Terumo Kabushiki Kaisha, Tokyo, Japan

[21] Appl. No.: 792,741

[22] Filed: Oct. 30, 1985

[30] Foreign Application Priority Data

Nov. 6, 1984 [JP] Japan .................................. 59-233769

[51] Int. Cl.⁴ ............................................. A61M 25/00
[52] U.S. Cl. ..................................... 604/283; 604/905
[58] Field of Search ................. 604/28, 29, 280, 283, 604/410, 411, 414, 415, 905, 177; 128/303 R; 136/272.6

[56] References Cited

U.S. PATENT DOCUMENTS

| 4,007,738 | 2/1977 | Yoshino | 604/410 |
| 4,289,337 | 9/1981 | Roe | 604/905 |
| 4,369,779 | 2/1983 | Spencer | 604/29 |
| 4,388,074 | 6/1983 | Seberg et al. | 604/177 |
| 4,412,834 | 11/1983 | Kulin et al. | 604/29 |
| 4,412,835 | 11/1983 | Spencer | 604/29 |
| 4,500,788 | 2/1985 | Kulin et al. | 604/29 |
| 4,569,736 | 2/1986 | Kosegaki et al. | 604/187 |

FOREIGN PATENT DOCUMENTS

| 2907832 | 9/1980 | Fed. Rep. of Germany | 604/283 |
| 2913676 | 10/1980 | Fed. Rep. of Germany | 136/272.6 |
| 3238299 | 12/1983 | Fed. Rep. of Germany | 128/303 R |
| 0069861 | 4/1982 | Japan | 604/280 |

Primary Examiner—C. Fred Rosenbaum
Assistant Examiner—Jerome R. Smith, Jr.
Attorney, Agent, or Firm—Burns, Doane, Swecker & Mathis

[57] ABSTRACT

A medical instrument for transferring liquid therethrough is provided, comprising a connector of a rigid resin including a generally cylindrical portion having a passage extending throughout the connector and one open end, the cylindrical portion at said one open end including a recess extending circumferentially and axially from the open end, the outside surface of the recess being provided with at least one substantially circumferential rib; and a tube of a flexible resin inserted into the recess and bonded thereto with an adhesive to define a continuous passage communicating the connector and the tube. The connector is formed of a resin which is difficult to bond with a curable adhesive and having a Shore D hardness of at least 55, the tube is formed of a flexible resin which is bondable with a curable adhesive and having a Shore D hardness of not higher than 45, and the joint portions of the connector and the tube are bonded with a ultraviolet-curable adhesive which shows a Shore D hardness of at least 70 after curing.

7 Claims, 2 Drawing Figures

MEDICAL INSTRUMENT

BACKGROUND OF THE INVENTION

This invention relates to a medical instrument comprising a connector of a rigid resin difficult to bond with a curable adhesive and a tube of a flexible resin bondable with such a curable adhesive wherein the connector and the tube are joined to form a continuous passage for transferring liquid through the instrument.

In general, most medical instruments for transferring liquid therethrough include a plurality of parts of different materials which are bonded one another. One such example is a winged venous infusion needle assembly. A needle is secured in a connector of rigid polypropylene resin which is, in turn, bonded or connected to a tube of flexible polyvinyl chloride resin with an adhesive of solvent type using, for example, tetrahydrofuran (THF) and methyl ethyl ketone (MEK).

Materials difficult to bond with adhesive, for example, polypropylene must be subject to a plasma treatment for sealing. Such plasma treatment is carried out by exciting oxygen gas or laughing gas in vacuum by high frequency discharge, applying the thus created plasma to a surface of the difficult-to-bond material to form active radicals such as carboxyl and carbonyl radicals on the surface. The thus activated surface enables adhesive bonding.

The use of solvent-type adhesive, however, gives rise to a number of problems. (1) Solvent attacks parts to be bonded which become brittle or weak and will eventually be broken. (2) Some material is dissolved from parts by solvent and will undesirably block a flowpath. (3) Residual solvent leaves the risk of toxicity. Medical instruments having parts bonded with such solvent-type adhesive suffer from these and other problems. There is the need for a technique capable of bonding parts without using an organic solvent.

Japanese Patent Application No. 58-199699 filed on Oct. 25, 1983 in the name of Terumo Kabushiki Kaisha proposed a medical instrument for transferring liquid therethrough, comprising a connector of a rigid resin including a generally cylindrical portion having a passage extending throughout the connector and one open end, the cylindrical portion at the one open end including an outer sleeve and an inner sleeve defining therebetween a recess extending circumferentially and axially from the open end, the inside surface of the outer sleeve being provided with at least one substantially circumferential rib; and a tube of a flexible resin inserted into the recess and bonded thereto with an adhesive to define a continuous passage communicating the connector and the tube. The present invention is a further improvement in a medical instrument of this type.

SUMMARY OF THE INVENTION

An object of the present invention is to provide a medical instrument comprising a connector of a rigid resin difficult to bond with a curable adhesive and a tube of a flexible resin bondable with such a curable adhesive wherein the members are joined with an adhesive having a cured hardness compatible with the hardness of the members instead of a conventional solvent-type adhesive, thereby achieving a firm bond between the members.

According to the present invention which attains the above object, there is provided a medical instrument for transferring liquid therethrough, comprising a connector of a rigid resin including a genrally cylindrical portion having a passage extending throughout the connector and one open end. The cylindrical portion at the one open end includes an outer sleve and an inner sleeve defining therebetween a recess extending circumferentially and axially from the open end. The inside surface of the outer sleeve is provided with at least one substantially circumferential rib. A tube of a flexible resin is inserted into the recess and bonded thereto with an adhesive to define a continuous passage communicating the connector and the tube. The connector is formed of a resin which is difficult to bond with a curable adhesive and having a Shore D hardness of at least 55. The tube is formed of a flexible resin which is bondable with a curable adhesive and having a Shore D hardness of not higher than 45. The joint portions of the connector and the tube are bonded with a ultraviolet-curable adhesive which shows a Shore D hardness of at least 70 after curing.

The Shore D hardness used herein is as defined by ASTM D 2240.

Preferably, the outside surface of the inner sleeve is tapered.

The medical instrument as assembled is preferably exposed to γ-rays to effect both curing and sterilization at the same time.

BRIEF DESCRIPTION OF THE DRAWING

The above and other objects, features, and advantages of the present invention will be more readily understood by reading the following description taken in conjunction with the accompanying drawing, in which.

DETAILED DESCRIPTION OF THE PREFERRED EMBODIMENTS

The liquid transferring medical instrument to which the present invention is applicable is a medical instrument wherein a connector of a rigid resin difficult to bond with a curable adhesive and a tube of a flexible resin bondable with such curable adhesive are joined to form a continuous passage throughout the instrument and which finds applications as a winged venous infusion needle and a dialyzing indwelling needle assembly.

The basic concept of the present invention is to provide a safe liquid transferring medical instrument by joining two members with a ultraviolet-curable adhesive having a proper cured hardness compatible with the hardness of the joined members without using a conventional solvent-type adhesive and without a plasma treatment.

The term ultraviolet curable adhesive used herein means that the adhesive will cure or harden upon exposure to electromagnetic radiation of ultrashort wave such as ultraviolet rays and γ-rays for a certain period of time.

Although the bonding or joining of a connector of a rigid resin difficult to bond with a curable adhesive with a tube of a flexible resin bondabale with such a curable adhesive as used in a winged infusion needle assembly is described as one preferred embodiment of the present invention, it should, of course, be understood that the present invention is not limited to the illustrated embodiment. The term difficult-to-bond means that the use of the adhesive alone cannot produce a sufficient bond strength to withstand in practical use.

Figure 1:
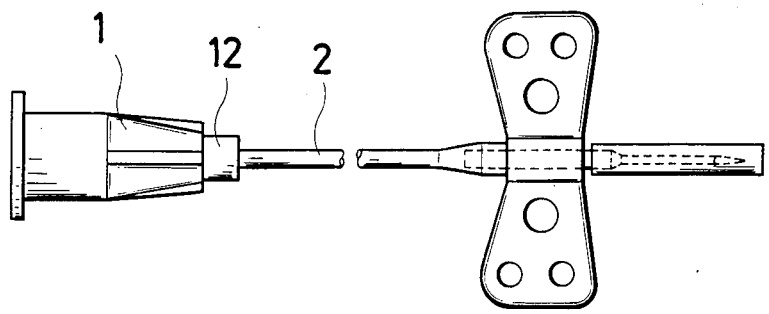
FIG. 1 is a plan view of a typical winged venous infusion needle assembly to which the present invention is applied.

FIG. 1 shows an overall winged infusion needle assembly as a typical example of the medical instrument to which the present invention is applicable. The present invention is not limited to the winged infusion needle assembly, but applicable to any medical instrument.

Figure 2:
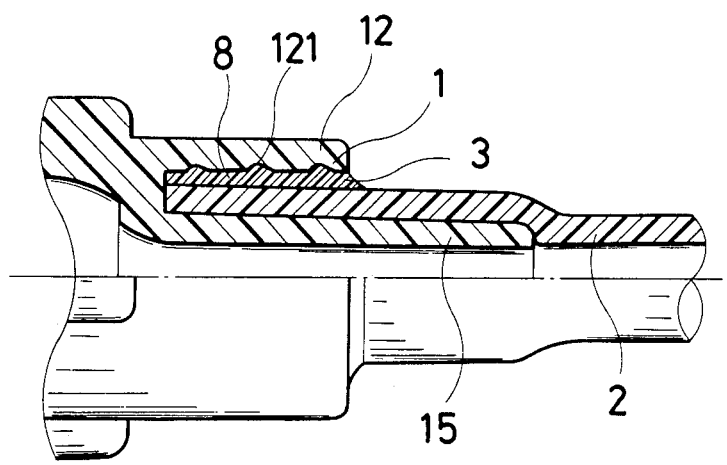
FIG. 2 is an elevation of one embodiment of the medical instrument of the present invention, with upper half being shown in cross section.

FIG. 2 illustrates a medical instrument which is a connector portion of the winged infusion needle assembly. The medical instrument comprises two tubular members joined. More illustratively, a connector 1 of a rigid resin has a Luer tapered connection to which a tube 2 of a flexible resin is joined.

The connector 1 is formed of a rigid resin having a Shore D hardness of at least 55. Examples of the rigid resins which are difficult to bond with a curable adhesive and have a Shore D hardness of at least 55 include polypropylene (PP), polyethylene (PE), and polyethylene terephthalate (PET), but are not limited thereto.

The tube 2 is formed of a flexible resin having a Shore D hardness of 45 or lower. Some nonlimiting examples of the flexible resins which are bondable with a curable adhesive and has a Shore D hardness of 45 or less include flexible polyvinyl chloride (PVC), vinyl chloride elastomers, and styrene elastomers. Only combinations of a resin having a hardness of lower than 45 (inclusive) with a resin haing a hardness of higher than 55 (inclusive) are contemplated herein and other combinations outside the above-defined hardness range are not successful in improving bond strength even when the adhesive used meets the requirement of the present invention.

The rigid resin connector 1 and the flexible resin tube 2 are joined and bonded with a ultraviolet (UV) curable adhesive 3. The UV curable adhesives used herein should have a Shore D hardness of at least 70 after curing. A sufficient bond strength cannot be obtained when the hardnesses of the members to be joined and the adhesive do not fall within the above defined range. A significantly increased bond strength is obtained only when the adhesive has a cured hardness of 70 or higher.

Some nonlimiting examples of the UV curable resins include polyester acrylate, epoxy acrylate, and polyurethane acrylate resins.

In the illustrated embodiment, the connector 1 of rigid resin includes a generally cylindrical portion having a passage or bore extending throughout the connector. The cylindrical portion is open at one end and includes an outer sleeve 12 and an inner sleeve 15 surrounded by and spaced apart from the outer sleeve 12. The outer and inner sleeves 12 and 15 thus define a circumferentially and axially extending recess 8 therebetween. The inner sleeve 15 is inserted into the tube 2. The outside surface of the inner sleeve 15 is slightly tapered and has a diameter slightly larger than the tube 2. The radial distance of the recess should be greater than the wall thickness of the flexible resin tube 2.

The inside surface of the outer sleeve 12 is formed with at least one circumferential rib or groove 121. The flexible resin tube 2 is inserted in the recess 8, that is, fitted over the inner sleeve 15 in the illustrated embodiment. A gap is left between the flexible tube 2 and the ribbed inside surface of the outer sleeve 12 and then filled with the UV-curable adhesive 3. The adhesive may also be applied to the inner sleeve 15 before the tube is fitted. The assembly is then exposed to UV or γ-radiation to cure the adhesive.

In this way, the rigid resin connector 1 is joined and bonded to the flexible resin tube 2. The UV cured adhesive fills in the gap between the inside surface of the connector outer sleeve 12 and the tube 2 and forms a biting engagement with the ribs 121 on the inside surface of the outer sleeve, providing an enhanced withdrawal resistance to form a firm bond between the connector and the tube.

The ribs or grooves 121 formed in the inside surface of the outer sleeve 12 of the connector 1 in order to provide a bond strength may take discontinuous multiple ring or continuous spiral form. The spiral rib is rather preferred because the UV-curable adhesive can fully fill the gap along the continuous channel.

Although the ribs 121 are formed on the outer sleeve 12 of the connector in the illustrated embodiment, they may also be formed on the outside surface of the inner sleeve 15. It has been found that a sufficient withdrawal resistance is achievable by providing such ribs or grooves on at least one of the recess-facing surfaces of the outer and inner sleeves.

The depth of the ribs or grooves is closely related to the mold releasability of the member and their number is closely related to the withdrawal resistance or bond strength achievable. The bond strength depends on the ratio of the surface area of outer or inner sleeve having a flat surface to that having a ribbed surface. It is found that a sufficient bond strength is obtained when the ratio ranges from 1:1.1 to 1:1.5, and preferably from 1:1.2 to 1:1.3. The ribs and grooves used herein are convex and concave surface portions of an irregularly configured surface, respectively.

As described above, the inner sleeve 15 of the rigid resin connector 1 has an outer diameter slightly larger than the inner diameter of the tube 4. This also contributes to an increased bond strength.

Since the assemblies or instruments prepared according to the present invention are intended for medical use, they are finally sterilized, for example, by ethylene oxide gas, autoclave, or γ-ray sterilization. Since the adhesive used is of UV curable type, γ-ray exposure is effective to carry out curing and sterilization at the same time.

In order to determine the effectiveness of the present invention, we carried out a number of experiments. Some are given below.

EXAMPLES

A number of assemblies were prepared by joining the rigid resin connector 1 and the flexible resin tube 2 as shown in FIG. 2. The outer sleeve 12 of the connector 1 was ribbed to give a joint surface area of 33 mm².

The following materials were used to form the connector and tube.

|  | Shore D hardness |
|---|---|
| Connector 1 | |
| 1-1 Polyethylene resin | 60 |
| 1-2 Polypropylene resin | 87 |
| Tube 2 | |
| 2-1 Polyvinyl chloride resin + 65 phr plasticizer | 25 |
| 2-2 Polyvinyl chloride resin + 55 phr plasticizer | 35 |
| 2-3 Polyvinyl chloride resin + | 40 |

-continued

| | Shore D hardness |
|---|---|
| 40 phr plasticizer | |

(phr = part per hundred parts of resin)

The adhesive used is a group of UV curable polyurethane acrylate adhesives commercially available from Toa Synthetic Chemicals K.K. The amount of adhesive applied was 2.0 mg.

| Adhesive 3 (Grade No.) | Shore D hardness after curing |
|---|---|
| 3-1 (3576K4) | 60 |
| 3-2 (3596) | 64 |
| 3-3 (3564K1) | 66 |
| 3-4 (3564K4) | 70 |
| 3-5 (3603) | 73 |
| 3-6 (3583) | 84 |

Using these materials, a set of 5 specimens was prepared for each of assemblies having different material combinations. The specimens were determined for bond strength using an Autograph DCS-100 tensile tester manufactured by Shimazu Mfg. K.K. operating at a pulling speed of 50 mm/min. Five measurements were averaged for each set.

The results are shown in Table 1.

TABLE 1

| Connector (Hardness) | Tube (Hardness) | Adhesive (Hardness) | Bond strength kg |
|---|---|---|---|
| 1-1 (60) | 2-1 (25) | 3-1 (60) | 2.0 |
| 1-1 (60) | 2-1 (25) | 3-2 (64) | 2.1 |
| 1-1 (60) | 2-1 (25) | 3-3 (66) | 2.1 |
| 1-1 (60) | 2-1 (25) | 3-4 (70) | 2.8 |
| 1-1 (60) | 2-1 (25) | 3-5 (73) | 2.6 |
| 1-1 (60) | 2-1 (25) | 3-6 (84) | 2.6 |
| 1-2 (87) | 2-2 (35) | 3-1 (60) | 2.0 |
| 1-2 (87) | 2-2 (35) | 3-2 (64) | 2.0 |
| 1-2 (87) | 2-2 (35) | 3-3 (66) | 2.1 |
| 1-2 (87) | 2-2 (35) | 3-4 (70) | 2.8 |
| 1-2 (87) | 2-2 (35) | 3-5 (73) | 2.7 |
| 1-2 (87) | 2-2 (35) | 3-6 (84) | 2.5 |
| 1-2 (87) | 2-3 (40) | 3-1 (60) | 2.1 |
| 1-2 (87) | 2-3 (40) | 3-2 (64) | 2.2 |
| 1-2 (87) | 2-3 (40) | 3-3 (66) | 2.2 |
| 1-2 (87) | 2-3 (40) | 3-4 (70) | 2.7 |
| 1-2 (87) | 2-3 (40) | 3-5 (73) | 2.7 |
| 1-2 (87) | 2-3 (40) | 3-6 (84) | 2.6 |

*Hardness in Shore D hardness is given in parenthesis. Hardness in adhesive column is the hardness of cured adhesive.

EFFECT OF THE INVENTION

The medical instrument of the present invention has the following benefits.

(1) Since conventional solvent-type adhesive is not used to bond parts through which liquid is to pass, all of the problems resulting from the solvent are eliminated, for example, deterioration of part material by solvent, blockage of a flowpath by dissolved material, and toxicity of residual solvent.

(2) Since a UV-curable adhesive is used instead of a conventional solvent-type adhesive, polyolefin resins which are inexpensive, but difficult to bond, for example, polypropylene and polyethylene can be used in the manufacture of liquid transferring medical instruments without any additional treatment such as plasma treatment, resulting in a considerable cost down.

(3) A choice of a UV-curable adhesive having a cured hardness compatible with the hardness of a connector and a tube to be joined ensures a firm bond.

(4) The use of a UV-curable adhesive having a cured hardness of 70 or higher brings about a critical increase of at least 20% in bond strength as demonstrated in Table 1.

(5) Exposure to γ-radiation can effect both sterilization and joint curing at the same time.

(6) In the preferred embodiment, the connector of difficult-to-bond resin is formed with ribs of a configuration haing mold releasability to provide an enhanced bond strength. Formation of a spiral rib rather than discontinuous ring-like ribs allows the adhesive to smoothly and fully fill over the ribbed surface because of easy escape of air, always providing a further enhanced bond strength.

What we claim is:

1. A medical instrument for transferring liquid therethrough, comprising
a connector of a rigid resin including a generally cylindrical portion having a passage extending throughout the connector and one open end, said cylindrical portion at said one open end including an outer sleeve and an inner sleeve defining therebetween a recess extending circumferentially and axially from the open end, the inside surface of said outer sleeve being provided with at least one substantially circumferential rib, and
a tube of a flexible resin inserted into said recess and bonded thereto with an adhesive to define a continuous passage communicating said connector and said tube, characterized in that
said connector is formed of a rigid resin which is difficult to bond with a curable adhesive and having a Shore D hardness of at least 55,
said tube is formed of a flexible resin which is bondable with a curable adhesive and having a Shore D hardness of not higher than 45, and
the joint portions of said connector and said tube are bonded with a ultraviolet curable adhesive which shows a Shore D hardness of at least 70 after curing.

2. A medical instrument according to claim 1 wherein the outside surface of said inner sleeve is tapered.

3. A medical instrument according to claim 1 or 2 which is sterilized with gamma radiation.

4. A medical instrument according to claim 1 which is a winged infusion needle assembly.

5. A medical instrument according to claim 1 wherein said rigid resin is selected from the group consisting of polypropylene, polyethylene, and polyethylene terephthalate.

6. A medical instrument according to claim 1 wherein said flexible resin is selected from the group consisting of flexible polyvinyl chloride, vinyl chloride elastomers, and styrene elastomers.

7. A medical instrument for transferring liquid therethrough, comprising:
a connector of a rigid resin including a generally cylindrical portion having a passage extending throughout the connector and one open end, said cylindrical portion at said one open end including an outer sleeve and inner sleeve defining therebetween a recess extending circumferentially and axially from the open end, the inside surface of said outer sleeve being provided with at least one substantially circumferential rib; and a tube of a flexible resin inserted into said recess and bonded thereto with an adhesive to define a continuous passage communicating said connector and said tube;

said connector being formed of a rigid resin which is difficult to bond with a curable adhesive and having a Shore D hardness of at least 55, wherein said rigid resin is selected from the group consisting of polypropylene, polyethylene, and polyethylene terephthalate;

said tube being formed of a flexible resin which is bondable with a curable adhesive and having a Shore D hardness of not higher than 45, wherein said flexible resin is selected from the group consisting of flexible polyvinyl chloride, vinyl chloride elastomers, and styrene elastomers; and the joint portions of said connector and said tube being bonded with an ultraviolet curable adhesive which shows a Shore D hardness of at least 70 after curing.

* * * * *

UNITED STATES PATENT AND TRADEMARK OFFICE
CERTIFICATE OF CORRECTION

PATENT NO. : 4,695,276
DATED : Sep. 22, 1987
INVENTOR(S) : Shinno et al

It is certified that error appears in the above-identified patent and that said Letters Patent is hereby corrected as shown below:

```
In column 2, line 1, amend "genrally" to --generally--;
             line 4, amend "sleve" to --sleeve--;
             line 65, amend "bondabale" to --bondable--.
In column 3, line 30, amend "haing" to --having--.
In column 6, line 12, amend "haing" to --having--.
```

Signed and Sealed this

Thirty-first Day of May, 1988

Attest:

DONALD J. QUIGG

*Attesting Officer*  *Commissioner of Patents and Trademarks*